(12) United States Patent
Matsumoto et al.

(10) Patent No.: US 10,070,991 B2
(45) Date of Patent: Sep. 11, 2018

(54) LACRIMAL DUCT TUBE

(71) Applicant: KANEKA CORPORATION, Osaka-shi, Osaka (JP)

(72) Inventors: Mariko Matsumoto, Settsu (JP); Hidekazu Miyauchi, Settsu (JP); Eiji Ogino, Settsu (JP); Chihiro Koga, Settsu (JP)

(73) Assignee: KANEKA CORPORATION, Osaka-shi (JP)

( * ) Notice: Subject to any disclaimer, the term of this patent is extended or adjusted under 35 U.S.C. 154(b) by 293 days.

(21) Appl. No.: 15/039,986

(22) PCT Filed: Nov. 19, 2014

(86) PCT No.: PCT/JP2014/080669
§ 371 (c)(1),
(2) Date: May 27, 2016

(87) PCT Pub. No.: WO2015/079999
PCT Pub. Date: Jun. 4, 2015

(65) Prior Publication Data
US 2017/0035610 A1    Feb. 9, 2017

(30) Foreign Application Priority Data
Nov. 28, 2013    (JP) ................. 2013-246052

(51) Int. Cl.
*A61F 9/007* (2006.01)
(52) U.S. Cl.
CPC .. *A61F 9/00772* (2013.01); *A61F 2250/0014* (2013.01)
(58) Field of Classification Search
CPC .................. A61F 2250/0014; A61F 9/00772
See application file for complete search history.

(56) References Cited

U.S. PATENT DOCUMENTS 6,270,477 B1 *  8/2001  Bagaoisan ....... A61B 17/12045
                                                604/102.01
6,458,867 B1 * 10/2002  Wang .................. A61L 29/085
                                                523/105
(Continued)

FOREIGN PATENT DOCUMENTS

JP          2539325 B2    10/1996
JP       2000-126221 A     5/2000
(Continued)

OTHER PUBLICATIONS

International Search Report, issued in PCT/JP2014/080669, dated Dec. 22, 2014.
(Continued)

*Primary Examiner* — Tatyana Zalukaeva
*Assistant Examiner* — Kai Weng
(74) *Attorney, Agent, or Firm* — Birch, Stewart, Kolasch & Birch, LLP

(57)            ABSTRACT

A lacrimal duct tube includes: a pair of tubular members that each have at one end an opening communicating with a lumen and have in a wall a hole for guiding a lacrimal duct tube operative instrument to the lumen; and a connection member that connects the other ends of the tubular members. Surfaces of the tubular members include a hydrophilic-coated portion and a non-coated portion without the hydrophilic coating. It is preferred that the lumen in the vicinity of the opening includes an engagement portion for engagement with a tip of the lacrimal duct tube operative instrument, and the non-coated portion is formed without overlapping with the surface of the tubular member at the position of the engagement portion. The lacrimal duct tube can be used favorably for various lacrimal duct obstruction treatments. In the case of using a sheath such as in sheath guided endoscopic probing, the lacrimal duct tube can be easily inserted into the sheath and be firmly fixed to the (Continued)

sheath. In the case of inserting the lacrimal duct tube directly into the lacrimal duct, the lacrimal duct tube can be easily passed through the lacrimal duct and be easily operated in the lacrimal duct.

15 Claims, 8 Drawing Sheets

(56) References Cited

U.S. PATENT DOCUMENTS

2006/0235367 A1 10/2006 Takashima et al.
2014/0364790 A1 12/2014 Matsumoto et al.

FOREIGN PATENT DOCUMENTS

| | | |
|---|---|---|
| JP | 2004-202276 A | 7/2004 |
| JP | 3558924 B2 | 8/2004 |
| JP | 2010-213957 A | 9/2010 |
| JP | 2011-200601 A | 10/2011 |
| JP | 2013-176488 A | 9/2013 |
| WO | WO 2004/060219 A1 | 7/2004 |
| WO | WO 2013/005004 A1 | 1/2013 |
| WO | WO 2013/111435 A1 | 8/2013 |

OTHER PUBLICATIONS

Written Opinion of the International Searching Authority, issued in PCT/JP2014/080669, dated Dec. 22, 2014.

* cited by examiner

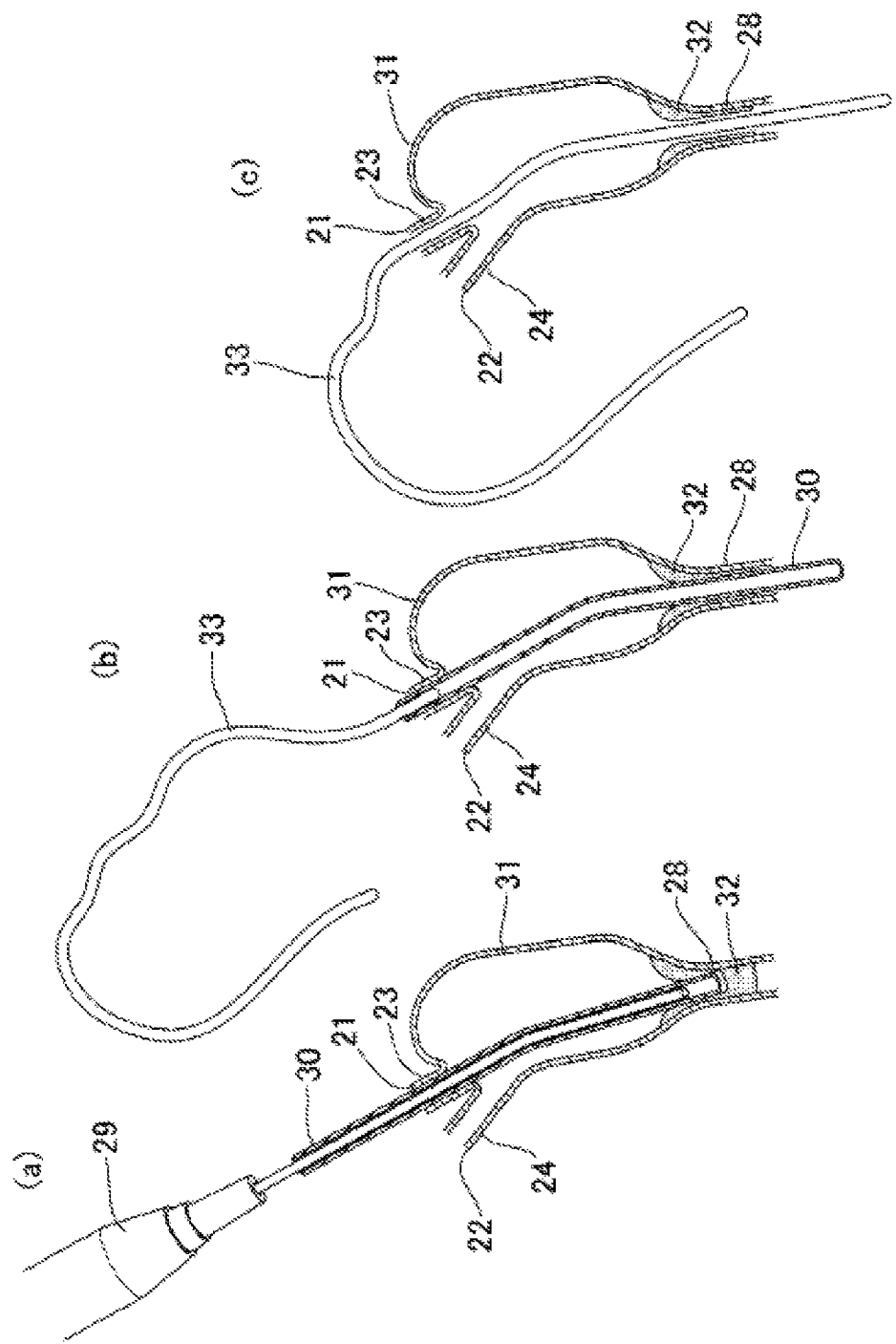
[Fig. 1]

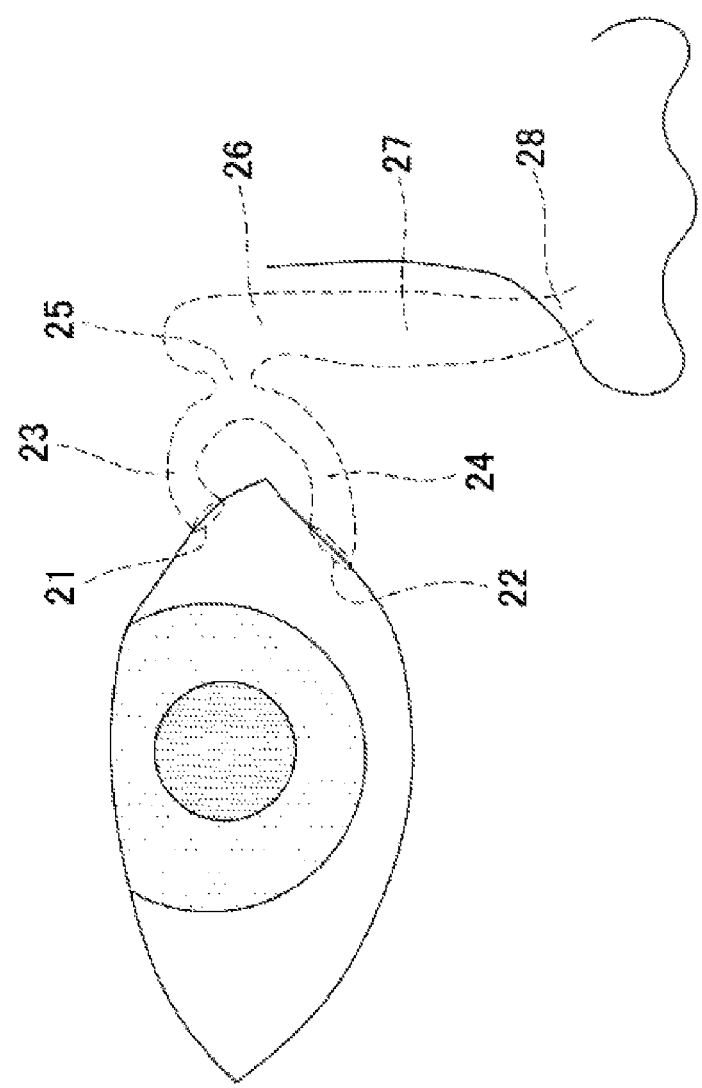
[Fig. 2]

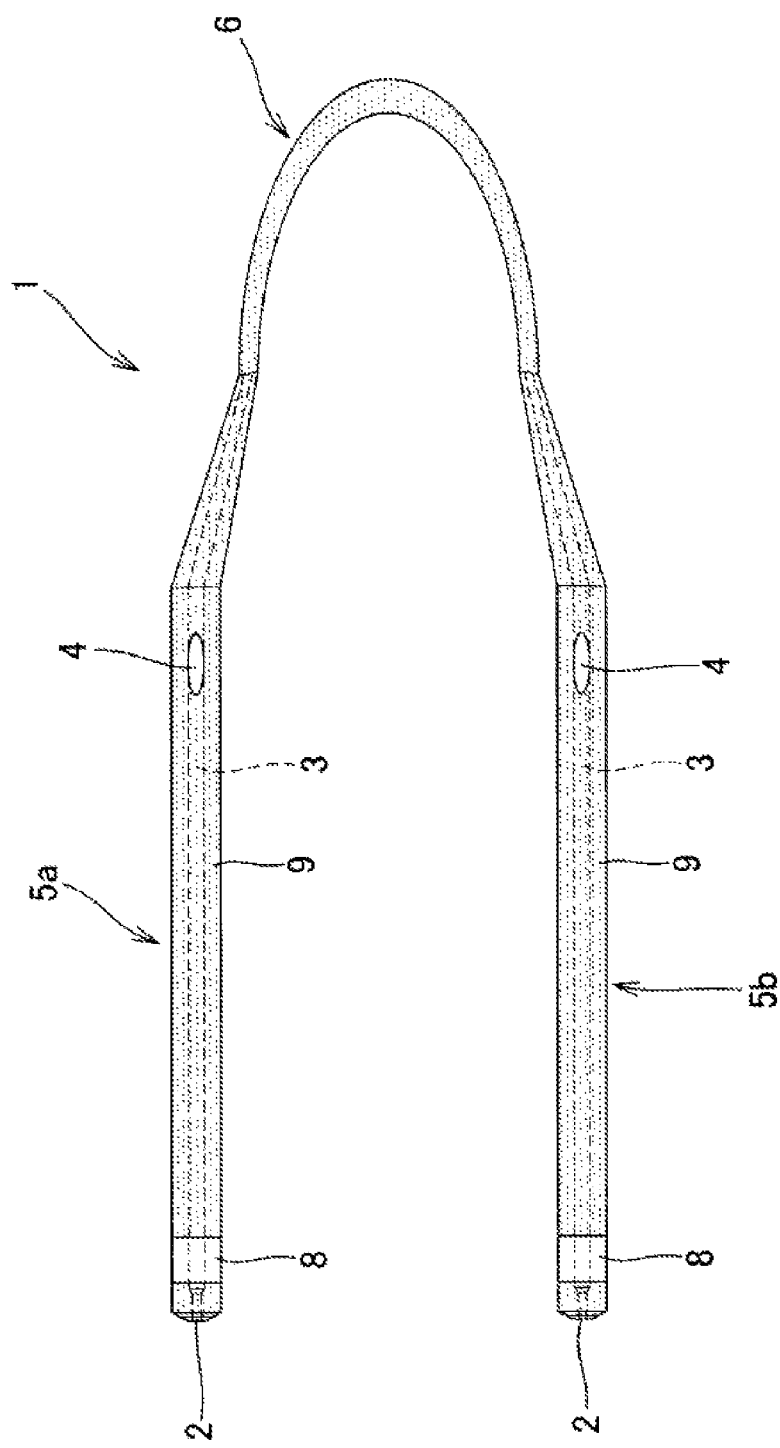

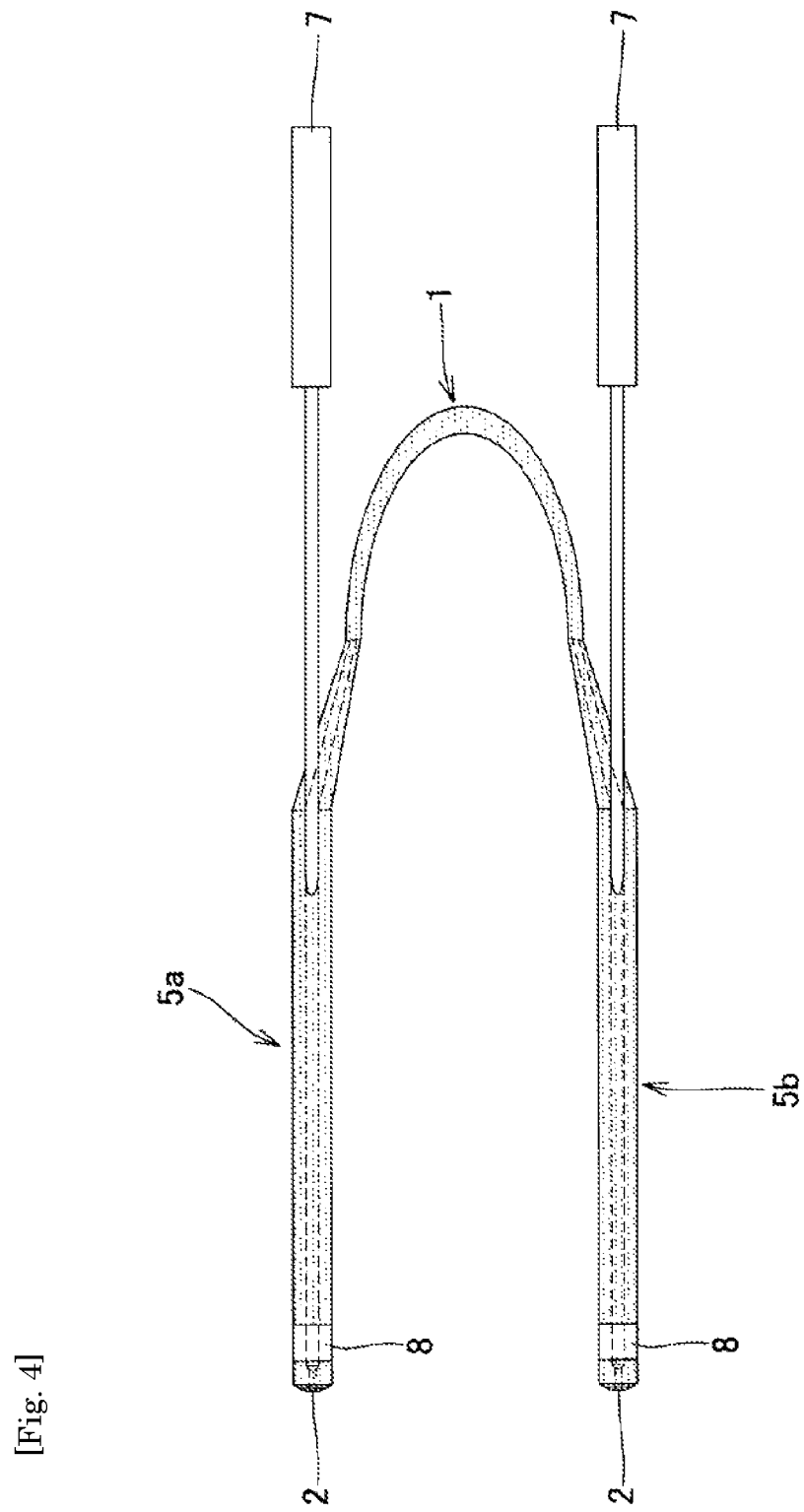
[Fig. 4]

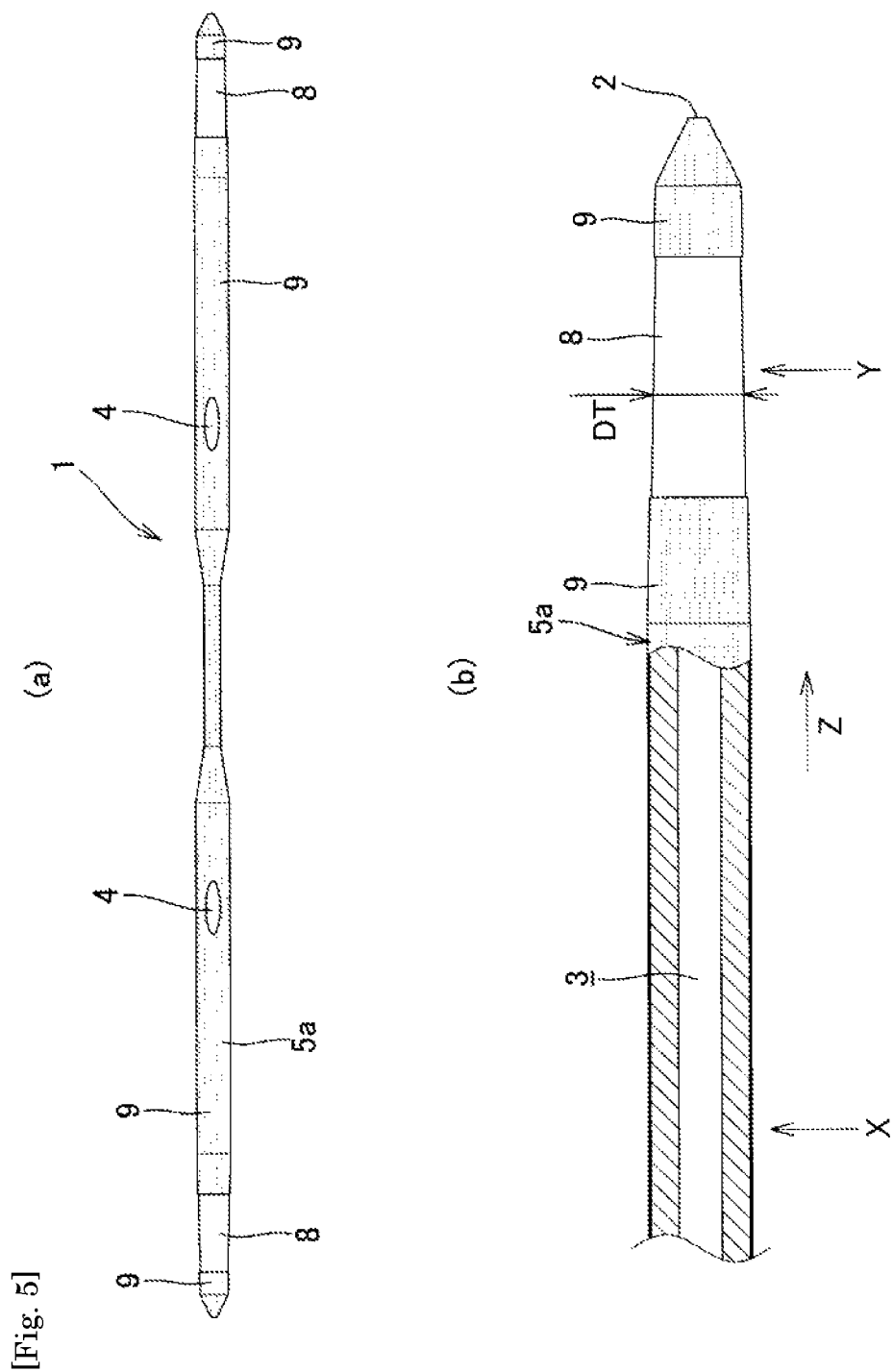

[Fig. 6]
(a)
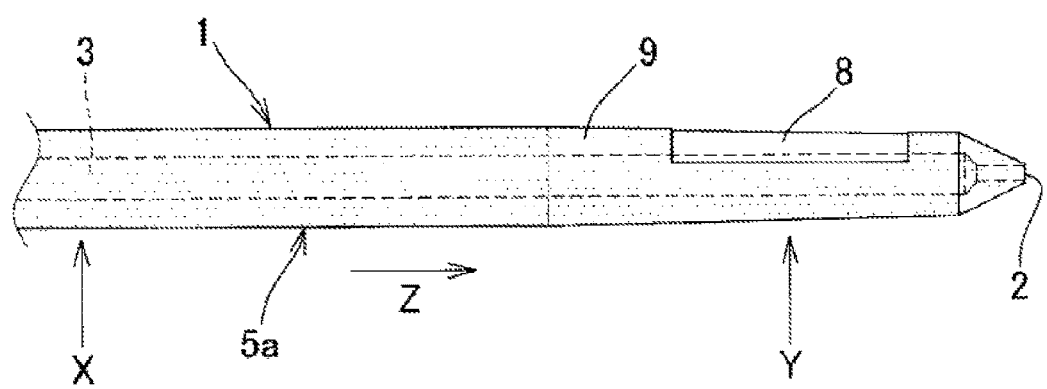
(b)
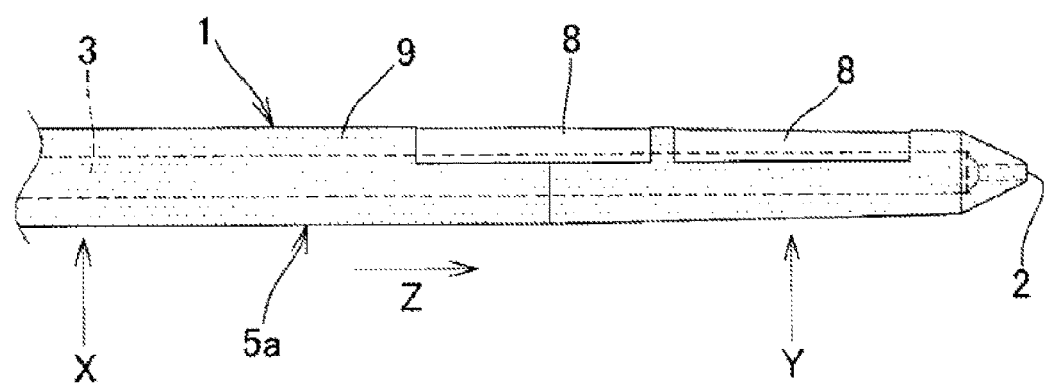

[Fig. 7]
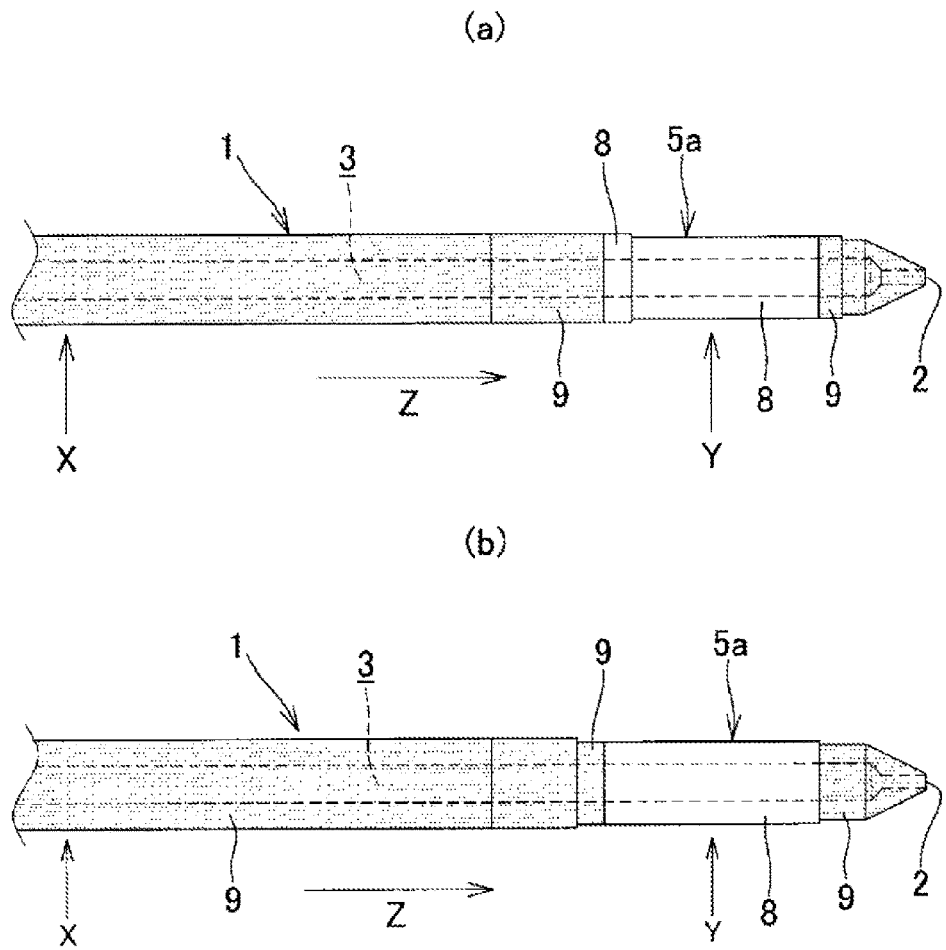
[Fig. 8]
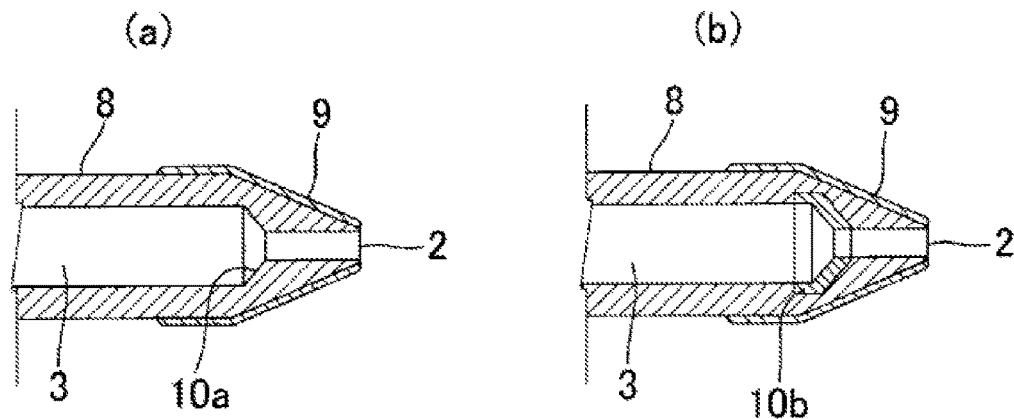

[Fig. 9]
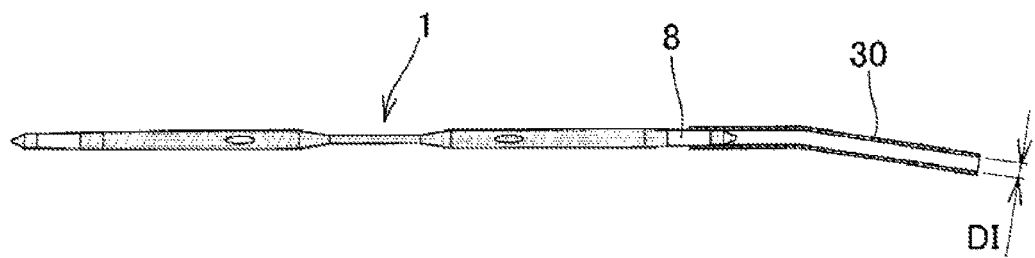
[Fig. 10]
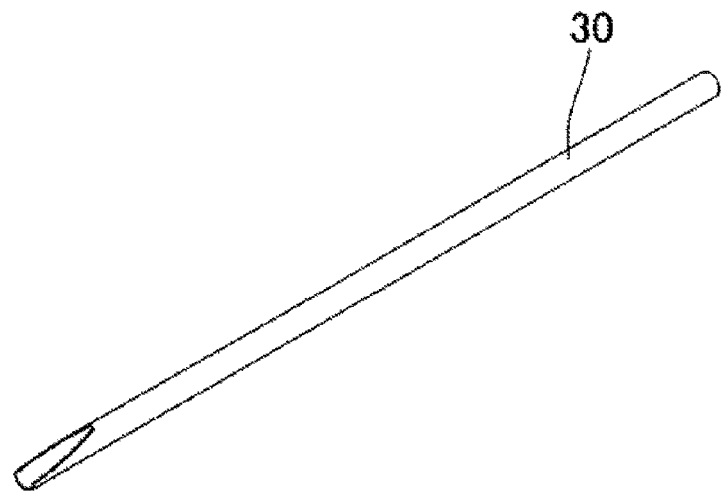

LACRIMAL DUCT TUBE

TECHNICAL FIELD

The present invention relates to a lacrimal duct tube for use in treatment of lacrimal duct obstruction.

BACKGROUND ART

Treatment methods for lacrimal duct obstruction resulting in epiphora include: (i) probing by a lacrimal duct bougie, (ii) placement of a lacrimal duct tube; (iii) dacryocystorhinostomy (DCR); (iv) lacrimal canaliculization; (v) nasolacrimal duct plastic surgery; (vi) lacrimal caruncle moving surgery, and the like.

The probing by the lacrimal duct bougie in (i) is intended to insert a narrow tube called bougie into a lacrimal duct to open an obstructed site and reconstruct a flow path for a lacrimal fluid. The lacrimal duct tube (ii) to be used after the probing is a lacrimal duct intubation instrument that is placed in the lacrimal duct to maintain the flow path and reconstruct the tissues. These methods are conducted as first treatments in many cases due to their ease of treatment and minimal invasiveness. Meanwhile, the treatments (iii) dacryocystorhinostomy (DCR), (iv) lacrimal canaliculization, (v) nasolacrimal duct plastic surgery, and (vi) lacrimal caruncle moving surgery are highly effective but relatively invasive because of the need for incisions in a patient's face or drilling holes in bones, and thus are conducted a last resort.

After the probing by the lacrimal duct bougie (i), the lacrimal duct tube for use in the treatment method (ii) is placed in the lacrimal duct for maintaining of the flow path and reconstruction of the tissues. The placement of the lacrimal duct tube (ii) is easy, less invasive, and highly effective as compared to the foregoing treatment methods (iii) to (vi). Among such instruments, there is widely used a lacrimal duct tube in which its central part is formed by a narrow and soft tube or rod and its both sides are formed by hard and thick tubes, as disclosed in Patent Document 1 (for example, refer to Patent Documents 1, 2, and 3).

The lacrimal duct tube includes a tube and a pair of bougies that is inserted into the tube from apertures at both sides of the tube, and the bougies are operated to guide the tube into a lacrimal duct and place the tube there. As shown in FIG. 2 of Patent Document 1, the lacrimal duct includes lacrimal puncta (21 and 22), lacrimal canaliculi (23 and 24), a lacrimal sac (26), a nasolacrimal duct (27), and others. The lacrimal duct tube is inserted into the lacrimal duct.

However, to insert the lacrimal duct tube, it is necessary to grope for intra-lacrimal duct operations. The bougies are blindly operated and thus may break through the tube or make a hole at a site other than in the normal lacrimal duct (creating a false passage), which results in poor therapeutic outcomes.

In addition, in the field of lacrimal duct obstruction treatment, surgeries based on sheath guided endoscopic probing have been newly conducted in recent years. This technique is excellent in that a sheath as an outer casing made of Teflon (registered trademark) or polyurethane covering a lacrimal endoscope precedes the lacrimal endoscope in the lacrimal duct to observe from behind that the tip of the sheath opens the obstructed site in the lacrimal duct, and the sheath can be used as a guide for insertion of the tube to achieve exact tube insertion. Specifically, as shown in FIG. 1(a), a sheath 30 attached to a lacrimal endoscope 29 is inserted into an obstructed site 32 in an inferior nasal meatus 28 of the lacrimal duct 31 from an upper lacrimal punctum 21 through an upper lacrimal canaliculus 23 and passed through the obstructed site 32, and then the lacrimal endoscope 29 is removed. Next, as shown in FIG. 1(b), a lacrimal duct tube 33 is connected to the sheath 30, and the sheath 30 is pulled from the side opposite to the connection side of the lacrimal duct tube 33 to let the lacrimal duct tube 33 pass through the lacrimal duct 31. Next, as shown in FIG. 1(c), the sheath 30 is removed to place the lacrimal duct tube 33 in the lacrimal duct 31.

Next, although not shown, another sheath 30 attached to the lacrimal endoscope 29 is inserted into the obstructed site 32 in the inferior nasal meatus 28 of the lacrimal duct 31 from the lower lacrimal punctum 22 not to be put in the lacrimal duct tube 33 through the lower lacrimal canaliculus 24 and passed through the obstructed site 32, and then the lacrimal endoscope 29 is removed. Then, an end of the lacrimal duct tube 33 not passing through the obstructed site 32 is connected to the sheath 30, and the sheath 30 is pulled from the side opposite to the connection side of the lacrimal duct tube 33 to let the other end of the lacrimal duct tube 33 pass through the lacrimal duct 31. Lastly, the sheath 30 is removed to place the lacrimal duct tube 33 in the lacrimal duct 31.

However, the foregoing method needs to include the step of connecting the sheath 30 inserted into the patient's lacrimal duct and the lacrimal duct tube 33. In addition, occurrence of the disconnection between the sheath 30 and the lacrimal duct tube 33 could result in an unsuccessful surgery. In actuality, a wide variety of sheaths different in inner diameter and material are used. To ensure reliable procedure and reduction in complexity, the lacrimal duct tube needs to be capable of smooth insertion into the holes of sheaths of various materials, firm connection and adherence to the sheath during surgeries, and smooth operation in the lacrimal duct.

Meanwhile, instead of using the sheath, a lacrimal endoscope may be inserted into the lacrimal duct tube. For example, there is known a lacrimal duct treatment tool including: a lacrimal duct placement main body that has an outer diameter allowing insertion into the lacrimal duct and is formed of a flexible material; and a sheath part that is provided at the lower end of the lacrimal duct placement main body and is composed of a flexible cylindrical body formed of a harder material than that for the lacrimal duct placement main body (refer to Patent Document 4).

However, in the case of using the lacrimal duct treatment tool in the sheath guided endoscopic probing, the lacrimal duct treatment tool is long and is likely to be difficult to operate in general. In addition, it is necessary to separate the main body and the sheath part of the lacrimal duct treatment tool after placement in the lacrimal duct.

As described above, various methods for lacrimal duct obstruction treatment are currently employed, but it cannot be said that lacrimal duct tubes usable for any lacrimal duct obstruction treatment have been sufficiently developed, and the current lacrimal duct tubes have room for improvement.

CITATION LIST

Patent Literatures

Patent Document 1: Japanese Patent No. 2539325
Patent Document 2: Japanese Patent No. 3558924
Patent Document 3: JP-A No. 2004-202276
Patent Document 4: JP-A No. 2010-213957

SUMMARY OF INVENTION

Technical Problem

In light of the foregoing circumstances, an object of the present invention is to provide a lacrimal duct tube that can be used favorably for various lacrimal duct obstruction treatments, specifically, a lacrimal duct tube that, in the case of using a sheath such as in sheath guided endoscopic probing, can be easily inserted into the sheath and be firmly fixed to the sheath, and in the case of inserting the lacrimal duct tube directly into the lacrimal duct, can be easily passed through the lacrimal duct and be easily operated in the lacrimal duct.

Solution to Problem

The inventors have earnestly conducted studies with the aim of solving the foregoing problems. As a result, the inventors have focused on the structure of the surface of the tubular member constituting the lacrimal duct tube, and revealed that, by providing the lacrimal duct tube with a hydrophilic-coated portion and a non-coated portion without hydrophilic coating, the lacrimal duct tube could be easily inserted into the sheath and firmly fixed to the sheath in the sheath guided endoscopic probing, and when being inserted directly to the lacrimal duct, the lacrimal duct tube could be favorably passed through the lacrimal duct and operated in the lacrimal duct, thereby completing the present invention.

Specifically, the gist of the present invention is as follows:

[1] A lacrimal duct tube, including: a pair of tubular members that each have at one end an opening communicating with a lumen and have in a wall a hole for guiding a lacrimal duct tube operative instrument to the lumen; and a connection member that connects the other ends of the tubular members, wherein surfaces of the tubular members include a hydrophilic-coated portion and a non-coated portion without the hydrophilic coating.

[2] The lacrimal duct tube according to [1], wherein the lumen in the vicinity of the opening includes an engagement portion for engagement with a tip of the lacrimal duct tube operative instrument, and the non-coated portion is formed without overlapping with the surface of the tubular member at the position of the engagement portion.

[3] The lacrimal duct tube according to [2], wherein the engagement portion is formed of a resin as a part of material for the tubular member or a material different from the resin, and has an inner diameter smaller than the outer diameter of the tip of the lacrimal duct tube operative instrument.

[4] The lacrimal duct tube according to any of [1] to [3], wherein the non-coated portion is partially or entirely formed at 12 mm or less from the one end of the tubular member.

[5] The lacrimal duct tube according to any of [1] to [4], wherein the outer diameter of the non-coated portion of the tubular member is 1.0 to 1.7 mm.

[6] The lacrimal duct tube according to [5], wherein the outer diameter of the non-coated portion of the tubular member is 1.2 to 1.4 mm.

[7] The lacrimal duct tube according to any of [1] to [6], wherein the non-coated portion overlaps the tubular member at a position of 3 mm from the one end of the tubular member.

[8] The lacrimal duct tube according to any of [1] to [7], wherein the non-coated portion extends over the entire or partial periphery of the tubular member.

[9] The lacrimal duct tube according to any of [1] to [8], wherein at least part of the tubular member at the non-coated portion is narrowed toward the one end of the tubular member.

[10] The lacrimal duct tube according to [9], wherein the tubular member at the hydrophilic-coated portion adjacent to the non-coated portion is narrowed toward the one end of the tubular member.

[11] The lacrimal duct tube according to [10], wherein the tubular member is narrowed at both the non-coated portion and the hydrophilic-coated portion positioned at the other end side of the non-coated portion, and at the narrowed tubular member, the entire length of the hydrophilic-coated portion is longer than the entire length of the non-coated portion.

[12] The lacrimal duct tube according to any of [1] to [11], wherein the maximum outer diameter of the tubular member is 1.4 to 1.7 mm.

[13] The lacrimal duct tube according to any of [1] to [12], wherein the hole is an insertion opening for an operating bar as the lacrimal duct tube operative instrument or a lacrimal endoscope as the lacrimal duct tube operative instrument.

[14] The lacrimal duct tube according to any of [1] to [13], wherein, when the one end of the tubular member is inserted into an opening end of a sheath, the non-coated portion and a lumen wall of the sheath engage with each other, and the lacrimal duct tube reaches an obstructed site in a lacrimal duct in conjunction with movement of the sheath and is placed in the obstructed site.

[15] The lacrimal duct tube according to [14], wherein an inner diameter (DI) of the lumen of the sheath and an outer diameter (DT) of the tubular member at the non-coated portion satisfy the following relational expression (1):

$$1.00 \leq DT/DI \leq 1.89 \tag{1}$$

[16] The lacrimal duct tube according to [15], wherein the DI and the DT satisfy the following relational expression (2):

$$1.20 \leq DT/DI \leq 1.56 \tag{2}$$

Advantageous Effects of Invention

The lacrimal duct tube in the present invention uses the pair of tubular members each having at the one end the opening communicating with the lumen and the hole in the wall guiding the lacrimal duct tube operative instrument to the lumen. Accordingly, the lacrimal duct tube can be inserted into a sheath in the sheath guided endoscopic probing and can also be inserted directly into the lacrimal duct. In particular, the tip of an endoscope can be inserted from the hole up to the vicinity of the opening to keep the field of view from the lacrimal endoscope through the opening, as compared to a lacrimal duct tube with one end as a blind end. This allows the user to learn surely the status of the path through which the tube is passed, and prevent the problem that the tube generates a false passage to injure mucus membranes and the like and cause bleeding.

In addition, by providing the hydrophilic-coated portion on the surfaces of the tubular members, the lacrimal duct tube can be favorably inserted into the sheath and the lacrimal duct and favorably operated in the lacrimal duct. Further, by providing the non-coated portion on the surfaces of the tubular members, the lacrimal duct tube can be firmly fixed to the sheath when being inserted into the sheath.

BRIEF DESCRIPTION OF THE DRAWINGS

FIGS. 1(a) to 1(c) are schematic illustrative diagrams showing an example of a surgery on a lacrimal duct obstructed site according to the sheath guided endoscopic probing;

FIG. 2 is an illustrative diagram showing an anatomical structure of a lacrimal duct;

FIG. 3 is a schematic diagram showing an example of a lacrimal duct tube of the present invention;

FIG. 4 is a schematic diagram illustrating the state in which operating bars as bar-like operative instruments are inserted into the lacrimal duct tube shown in FIG. 3;

FIGS. 5(a) and 5(b) are a schematic diagram showing an example of the lacrimal duct tube of the present invention and a schematic diagram of tubular members;

FIGS. 6(a) and 6(b) are schematic diagrams of tubular members showing an example of the lacrimal duct tube of the present invention;

FIGS. 7(a) and 7(b) are schematic diagrams of tubular members showing an example of the lacrimal duct tube of the present invention;

FIGS. 8(a) and 8(b) are cross-sectional views of a tubular member in the vicinity of one end showing an example of the lacrimal duct tube of the present invention;

FIG. 9 is a cross-sectional diagram showing an example of the state in which the lacrimal duct tube of the present invention is inserted into a sheath; and FIG. 10 is a schematic diagram showing the state of a sheath used in an Experimental Example described later.

DESCRIPTION OF EMBODIMENTS

The present invention will be described later in detail.

Lacrimal duct referred to in the present invention is a duct (ocular adnexa) composed of upper/lower lacrimal puncta (21/22), upper/lower lacrimal canaliculi (23/24), a common canaliculus (25), a lacrimal sac (26), a nasolacrimal duct (27), a nasal tract (not shown), and Hasner's valve (not shown), as shown in FIG. 2, which is configured to guide a lacrimal fluid produced by a lacrimal gland (not shown) from an eye surface to an inferior nasal meatus (28). FIG. 2 is a diagram schematically showing an anatomical structure of a lacrimal duct. In addition, the duct extending from the upper lacrimal punctum (21) through the upper lacrimal canaliculus (23), and the common canaliculus (25) to the inferior nasal meatus (28) is referred to as an upper lacrimal duct, and the duct extending from the lower lacrimal punctum (22) through the lower lacrimal canaliculus (24), and the common canaliculus (25) to the inferior nasal meatus (28) is referred to as a lower lacrimal duct.

The lacrimal duct tube of the present invention is a tube placed in the lacrimal duct, and includes: a pair of tubular members that each have at one end an opening communicating with a lumen and have in a wall a hole for guiding a lacrimal duct tube operative instrument to the lumen; and a connection member that connects the other ends of the tubular members. The surfaces of the tubular members include a hydrophilic coated portion and a non-coated portion without the hydrophilic coating.

There is no particular limitation on the resin constituting the tubular members. The resin may be any one of resin compositions such as, but not limited to, silicone, polyamide elastomer, polyurethane, isobutylene copolymer, and a polymer alloy thereof, for example.

In the present invention, there is no particular limitation on the alloy. For example, in the case of using an alloy of polyurethane and isobutylene copolymer, the hardness of the tube can be adjusted by regulating the ratio between the isobutylene block copolymer (A) and the thermoplastic polyurethane resin (B). As the ratio of the thermoplastic polyurethane resin (B) to the isobutylene block copolymer (A) becomes higher, the hardness of the tube increases.

From the viewpoints of antithrombogenicity, surface smoothness, and flexibility, it is preferred that one weight % or more of the isobutylene block copolymer (A) is included (that is, the ratio of the isobutylene block copolymer (A) to the thermoplastic polyurethane resin (B) is (A)/(B)=1/99 to 99/1 by weight). Above all, from the viewpoint of abrasion resistance, the ratio of the isobutylene block copolymer (A) to the thermoplastic polyurethane resin (B) is preferably (A)/(B)=1/99 to 70/30 by weight. In particular, from the viewpoint of compression stress, the ratio of the isobutylene block copolymer (A) to the thermoplastic polyurethane resin (B) is preferably (A)/(B)=1/99 to 50/50 by weight. The resin composition for the integral tubes for use in the present invention may be composed only of the isobutylene block copolymer (A) and the thermoplastic polyurethane resin (B) or may be mixed with other components.

The isobutylene block copolymer (A) is preferably "SIBSTAR102T" produced by Kaneka Corporation, which is a styrene-isobutylene-styrene block copolymer (hereinafter, also called SIBS). The thermoplastic polyurethane resin (B) (hereinafter, also called TPU) is preferably "Miractran E385PNAT" produced by Nippon Miractran Co., Ltd. or "Tekotan TT1074A" produced by Lubrizol Corporation, which are ether aromatic cyclic polyurethanes, "Tecoflex EG100A" or "Tecoflex EG85A" produced by Lubrizol Corporation, which are ether alicyclic polyurethanes, or "Karubotan PC3575A" produced by Lubrizol Corporation, which is a polycarbonate polyurethane.

There is no particular limitation on the structure of the tubular members. The tubular members may be integral tubes composed of the same resin composition, may have a layered structure in which a plurality of layers different in kind of resin is stacked in the thickness direction, may have a column structure in which tubes of different resins are coupled together in the longitudinal direction, or may have a mixture of the layered structure and the column structure.

The lumen of the tubular member constitutes a space for accommodating a lacrimal duct tube operative instrument and the like inserted from the hole formed in the wall of the tubular member when the lacrimal duct tube is inserted into the lacrimal duct. In addition, the lumen of the tubular member constitutes a flow path for body fluids such as tears through the hole formed in the wall of the tubular member and the opening when the lacrimal duct tube is placed in the lacrimal duct.

The diameter and shape of the lumen are not particularly limited and may be the same as those of a commercial lacrimal duct tube.

The lumen may be provided with an engagement portion for engagement with the tip of the bar-like lacrimal duct tube operative instrument in the vicinity of the opening.

The engagement portion may have an inner diameter smaller than the outer diameter of the tip of the lacrimal duct tube operative instrument. The engagement portion may be formed of a resin as part of the material for the tubular member or may be formed of a material different from the resin.

The different material is not particularly limited and may be any of various hard resins or metals such as stainless steel. Stainless steel is preferred from the viewpoint of prevention of corrosion resulting from contact with body fluids, chemicals, or the like.

The engagement portion formed of the different material may be a reinforcement portion, for example. There is no particular limitation on the shape of the reinforcement portion. The reinforcement portion merely needs to be shaped to be placeable in the vicinity of the opening of the tubular member, ensure the field of view of a lacrimal endoscope inserted into the lumen of the tubular member, and serve as a stopper for the lacrimal endoscope. The reinforcement portion may be almost ring-shaped or the like.

Specifically, in the lacrimal duct tube, the almost ring-shaped engagement portion and the tubular member are arranged in a substantially concentric manner, and the engagement portion may have a cylindrical structure so as to be opened at both ends in the axial direction (aligned to the axial direction of the tubular member). There is no particular limitation on the cylindrical structure. For example, cylindrical structures employable for the lacrimal duct tube include: a structure in which the width vertical to the axial direction of the engagement portion and the tubular member decreases continuously from the other end to one end of the tubular member, for example, a structure in which the surface vertical to the axial direction reduces in diameter from the other end to one end of the tubular member, that is, having a tapered shape, or a structure in which the inner wall surface of the cylindrical structure reduces in diameter due to continuous changes in inclined angle to have a bowl shape, for example; a structure in which the width of the inner wall surface of the cylindrical structure continuously reduces; a structure in which the diameter of the inner wall surface continuously reduces; and a structure including a stepped portion in which the engagement portion and the tubular member are arranged in a concentric manner and the width of the engagement portion vertical to the axial direction of the engagement portion and the tubular member reduces stepwise, for example.

The engagement portion is positioned in the vicinity of the opening of the tubular member, at a predetermined distance from the openings. The predetermined distance is decided from the viewpoints of serving as a stopper for the lacrimal endoscope and ensuring the field of view of the lacrimal endoscope. For example, from the viewpoint of ensuring the field of view of the lacrimal endoscope, the lens at the tip of the lacrimal endoscope is preferably positioned at 2 mm or less from the terminal end of the opening of the tubular member. From the viewpoint of ensuring 70% or more of the field of view of the lacrimal endoscope, the lens at the tip of the lacrimal endoscope is preferably positioned at 1.5 mm or less, more preferably 1 mm or less. Therefore, from the viewpoint of ensuring the field of view of the lacrimal endoscope, the predetermined distance is preferably 2 mm or less, more preferably 1.5 mm or less, further more preferably 1 mm or less from the opening (terminal end of the opening).

The engagement portion can be formed by reducing the inner diameter of the tubular member at the one-end side in the vicinity of the opening using a mandrel with a predetermined outer diameter through heat processing. Alternatively, the inner diameter may be reduced by connecting another tubular member to the opening of the tubular member at the one-end side constituting the lacrimal duct tube of the present invention.

There is no particular limitation on the shape of the engagement portion. It merely needs to lock the bar-like operative instrument. For example, the cross section of the tubular member in the thickness direction may have a circular shape, a partially-chipped circular shape, or a shape with at least one protrusion toward the lumen.

The inner diameter of the tubular member at the engagement portion merely needs to be smaller than the diameter of the bar-like operative instrument. However, from the viewpoint of ensuring the sufficient field of view of the lacrimal endoscope, the inner diameter is preferably 0.50 to 0.90 mm, more preferably 0.65 to 0.86 mm.

As described above, the engagement portion is arranged in the vicinity of the opening at the one end of the tubular member at a predetermined distance from the opening, which allows the tubular member to be smoothly inserted into the lacrimal duct by the use of a force applied to the lacrimal endoscope with ensuring the field of view of the lacrimal endoscope. Further, the engagement portion such as a reinforcement portion serves as a stopper to reduce the risk of accidental penetration of the lacrimal endoscope from the opening. These effects can be further enhanced by adjusting the distance from the opening and the opening diameter of the opening as described above.

In addition, it is possible to, when the lacrimal endoscope is being used, recognize the path through which the tubular member is passed, and prevent the problem that the tube generates a false passage to injure mucous membranes and the like and cause bleeding.

The opening at the one end of the tubular member constitutes part of the flow path for body fluids such as tears when the lacrimal duct tube is placed in the lacrimal duct, and ensures the field of view of the lacrimal endoscope through the opening when the tip of the lacrimal endoscope inserted from the hole in the wall up to the vicinity of the opening. This prevents the problem that the tube generates a false passage to injure mucous membranes and the like and cause bleeding.

The size and shape of the opening are not particularly limited and may be the same as those of a commercial lacrimal duct tube. The range of the field of view of the lacrimal endoscope may be influenced by the diameter of the opening (in particular, the diameter of the opening at the one-end side) except for the viewing angle of the lacrimal endoscope, and therefore the diameter of the opening (also called opening diameter) is preferably as large as possible from the viewpoint of ensuring the field of view of the lacrimal endoscope. Meanwhile, when the opening diameter is larger, the thickness of the tubular member at the one-end side is smaller to make it difficult to hold the engagement portion. As a result, when the tubular member is inserted into the lacrimal duct by the use of a force applied to the lacrimal endoscope, the tip of the lacrimal endoscope may penetrate through the opening. Accordingly, the diameter of the opening (opening diameter) is preferably 0.5 to 0.8 mm, more preferably 0.65 to 0.75 mm from the viewpoints of holding the engagement portion, preventing penetration of the lacrimal endoscope, and ensuring the field of view of the lacrimal endoscope.

The hole in the wall of the tubular member constitutes part of a flow path for body fluids such as tears when the lacrimal duct tube is placed in the lacrimal duct, and constitutes an insertion opening for insertion of the lacrimal duct tube operative instrument and the like when the lacrimal duct tube is inserted into the lacrimal duct.

There is no particular limitation on the size of the hole as far as the lacrimal duct tube operative instrument can be inserted into the hole. However, the hole is preferably large to some extent because body fluids such as tears pass between the hole and the opening at the one end. In addition, there is no particular limitation on the shape of the hole and the shape may be circular, oval, square, polygonal, or the like. However, the oval shape may be preferred to reduce friction with the lacrimal endoscope.

The outer diameter of the tubular member merely needs to fall within the range in which it can be inserted into the lacrimal duct. For example, the tubular member with a maximum outer diameter of 1.4 to 1.7 mm is suitable for a wide range of patients' lacrimal ducts regardless of their nationalities and genders.

The lacrimal duct tube of the present invention is characterized in that the surface of the tubular member includes the hydrophilic-coated portion and the non-coated portion without the hydrophilic coating. Forming the hydrophilic-coated portion on the surface of the tubular member allows the lacrimal duct tube to be easily inserted into the sheath and the lacrimal duct and favorably operated in the lacrimal duct. Further providing the non-coated portion allows the lacrimal duct tube to be firmly fixed to the sheath when being inserted into the sheath. Accordingly, the lacrimal duct tube of the present invention is suitable to a wide variety of currently performed lacrimal duct obstruction treatments.

The hydrophilic coating for use in the hydrophilic-coated portion is intended to provide lubricity in contact with blood or tear fluid, reduce resistance at the time of insertion into the lacrimal duct, and realize favorable operability in the lacrimal duct. There is no particular limitation on the kind of the hydrophilic coating. Preferably, hydrophilic polymers such as poly(2-hydroxyethyl methacrylate), polyacrylamide, polyvinyl pyrrolidone, polyalkylene glycol, monomethoxy polyalkylene glycol, or blends of these polymers can be used.

There is no particular limitation on the position of the hydrophilic-coated portion. However, the hydrophilic-coated portion is preferably provided at the one-end side from the viewpoint of excellent insertability into the sheath and the lacrimal duct, and is preferably provided at the other-end side from the viewpoint of excellent operability in the lacrimal duct.

In the present invention, the non-coated portion refers to a surface portion of the tubular member without the hydrophilic-coated portion.

The non-coated portion merely needs to be provided within the range in which the tubular member at the one-end side can be inserted into the sheath.

For example, in the case where the lacrimal duct tube has the engagement portion, when the lacrimal duct tube is inserted into the sheath in the sheath guided endoscopic probing, the inner diameter of the sheath is smaller than the outer diameter of the lacrimal duct tube and the engagement portion and its surroundings are subjected to large pressure. However, by forming the hydrophilic-coated portion on the surface of the tubular member at a position with the engagement portion (engagement portion surface), the lacrimal duct tube can be smoothly inserted into the sheath. In addition, by forming the non-coated portion at a position without overlapping with the engagement portion surface, when the lacrimal duct tube is inserted into the sheath closer to the other end than the engagement portion surface, the lacrimal duct tube and the sheath can be firmly fixed to each other.

From the viewpoint of favorable applications to various kinds of sheaths and procedures, the non-coated portion is preferably partially or entirely formed at 12 mm or less from the one end of the tubular member.

Above all, when the non-coated portion is positioned at 3 mm from the one end of the tubular member, it has advantages that the tubular member and the sheath can engage with each other without excessively inserting the one end of the tubular member into the opening end of the sheath in the sheath guided endoscopic probing, and the tubular member does not come off from the sheath.

It is not necessary to provide the non-coated portion on the surface of the tubular member to which the sheath is not fitted. Accordingly, the hydrophilic-coated portion is provided on the surface of the tubular member at the side nearer the other end than the non-coated portion, which improves operability of the lacrimal duct tube in the lacrimal duct.

The non-coated portion may cover the entire or partial outer periphery of the tubular member without particular limitation on the range of the covering.

The outer diameter of the tubular member at the non-coated portion is preferably 1.0 to 1.7 mm, more preferably 1.2 to 1.4 mm from the viewpoints of easy fitting to the sheath used in the sheath guided endoscopic probing, hardness to come off from the sheath, and easy insertion into the lacrimal duct through the lacrimal punctum.

Regarding the shape of the tubular member including the non-coated portion, at least part of the tubular member with the non-coated portion is preferably narrowed toward the one end of the tubular member from the viewpoint of allowing the tubular member to be easily inserted into the sheath and the lacrimal duct.

As for the narrowed shape, for example, the tubular member with the non-coated portion may be partially or entirely tapered, stepped, or tapered and stepped.

Regarding the shape of the tubular member with the hydrophilic-coated portion adjacent to the non-coated portion, the tubular member with the hydrophilic-coated portion is also preferably narrowed toward the one end of the tubular member from the viewpoint of allowing the tubular member to be easily inserted into the lacrimal duct.

As for the narrowed shape, for example, the partial or entire tubular member with the hydrophilic-coated portion may be partially or entirely tapered, stepped, or tapered and stepped.

In the case where the tubular member with the non-coated portion and the tubular member with the hydrophilic-coated portion positioned at the side nearer the other end than the non-coated portion are both narrowed toward the end, by making the entire length of the hydrophilic-coated portion longer than the entire length of the non-coated portion, the lacrimal duct tube can be easily inserted directly into the lacrimal duct and favorably operated in the lacrimal duct in particular, thereby reducing the burdens on the patients.

In the present invention, when the inner diameter (DI) of the lumen of the sheath and the outer diameter (DT) of the tubular member with the non-coated portion satisfy the following relational expression (1):

$$1.00 \leq DT/DI \leq 1.89 \tag{1}$$

the tubular member is easy to be inserted into the sheath opening, and after the insertion, the sheath lumen wall and the surface of the non-coated portion of the tubular member are brought into sufficient contact with each other, and the lacrimal duct tube is not pushed back from the sheath.

When "DT/DI" is larger, the outer diameter of the tubular member with the non-coated portion is larger than the inner diameter of the lumen of the sheath, the lacrimal duct tube is difficult to be inserted into the sheath opening, and the lacrimal duct tube is pushed out from the sheath under a larger force. In contrast, when "DT/DI" is smaller, the outer diameter of the tubular member with the non-coated portion is smaller than the inner diameter of the lumen of the sheath, and the lacrimal duct tube is easy to be inserted into the sheath opening, but a non-contact part is likely to occur between the sheath lumen wall and the surface of the tubular member with the non-coated portion.

In addition, DT/DI preferably satisfies the following relational expression (2):

$$1.20 \leq DT/DI \leq 1.56 \tag{2}$$

and more preferably satisfies the following relational expression (3):

$$1.26 \leq DT/DI \leq 1.47 \qquad (3)$$

The sheath for use in the present invention merely needs to be composed of a transparent or translucent flexible cylindrical body of, for example, silicone, polyurethane, polyethylene, Teflon (registered trademark), or the like and be usable in lacrimal duct obstruction treatments.

The inner diameter of the sheath preferably falls within the range of 0.9 to 1.0 mm with consideration given to the relationship with the outer diameter of the tubular member to be inserted into the sheath.

The connection member is intended to connect the other ends of the two tubular members and merely needs to be smaller in diameter than the tubular member. The connection member merely needs to be composed of a flexible resin, and the resin may be any one of resin compositions such as, but not limited to, silicone, polyamide elastomer, polyurethane, isobutylene copolymer, and alloys thereof, for example.

The lacrimal duct tube operative instrument for use in the present invention refers to an instrument that is inserted into the lacrimal duct tube, and, when the lacrimal duct tube is inserted into the lacrimal duct and placed there, guides the lacrimal duct tube through the lacrimal duct, and then is removed from the lacrimal duct tube. An operating bar such as a bougie, for example, is applied to the lacrimal duct tube operative instrument. To insert the lacrimal duct tube into the lacrimal duct while visually observing the inside of the lacrimal duct, a lacrimal endoscope is used instead of the operating bar such as a bougie. The lacrimal endoscope is also applied to the lacrimal duct tube operative instrument.

There are no particular limitations on the operating bar and the lacrimal endoscope as far as they are usable for lacrimal duct obstruction treatments.

A plurality of embodiments of the lacrimal duct tube according to the present invention will be described below with reference to the drawings. However, the present invention is not limited to these embodiments.

FIG. 3 illustrates an example of an outer appearance of a lacrimal duct tube 1 in the present invention. The lacrimal duct tube 1 includes a pair of tubular members 5a and 5b each having an opening 2 at one end and a hole 4 in a side wall communicating with a lumen 3, and a connection member 6 that connects the other ends of the tubular members 5a and 5b.

In the lacrimal duct tube 1 of the embodiment, the tubular members 5a and 5b are connected to the connection member 6 narrower than the tubular members 5a and 5b.

As for the connection between the tubular members 5a, 5b and the connection member 6, to connect the outer resin materials of the tubular members 5a and 5b to the connection member 6, for example, the ends of the tubular members 5a and 5b opposite to the openings 2 are reduced in diameter, and the outer resin materials are closed at the endmost positions and are welded to the connection member 6. To connect the inner resin materials of the tubular members 5a and 5b to the connection member 6, the ends of the connection member 6 are inserted into the lumens of the tubular members 5a and 5b opposite to the openings 2, and the tubular members 5a, 5b and the connection member 6 are heated and welded to each other in the usual manner.

The tubular members 5a and 5b may have a cylindrical shape as shown in FIG. 3 or may have a shape narrowed toward a one-end side as shown in FIG. 5.

The maximum outer diameter of the tubular members 5a and 5b is preferably 1.4 to 1.7 mm.

FIG. 4 illustrates the state in which bar-like lacrimal duct tube operative instruments (operating bars) 7 are inserted from the holes 4 into the lacrimal duct tube 1 shown in FIG. 3. The holes 4 shown in FIGS. 3 and 4 have an oval shape. Alternatively, the holes 4 may be any of circular, square, or polygonal holes or incisions into which the bar-like lacrimal duct tube operative instruments 7 can be easily inserted.

The bar-like lacrimal duct tube operative instruments 7 include lacrimal endoscopes.

FIG. 5(a) shows an embodiment of the lacrimal duct tube 1 in the present invention, and FIG. 5(b) schematically shows the one-end side of the tubular member 5a. A non-coated portion 8 is provided on the surface of the tubular member 5a. The portion on the surface of the tubular member 5a other than the non-coated portion 8 constitutes a hydrophilic-coated portion 9 with hydrophilic coating.

The non-coated portion 8 may cover the entire outer periphery of the tubular member 5a as shown in FIGS. 5(a) and 5(b), or may cover the partial outer periphery of the tubular member 5a as shown in FIG. 6(a). In addition, two or more non-coated portions 8 may be formed as shown in FIG. 6(b).

As for the position of the non-coated portion 8, the non-coated portion 8 is preferably partially or entirely formed at 12 mm or less from the one end of the tubular member 5a. For example, referring to FIGS. 5(b), 6(a), and 6(b), when it is assumed that a position X is located at 12 mm from the one end of the tubular member 5a, FIG. 5(b) shows the state in which the entire non-coated portion 8 is formed at 12 mm or less from the one end, and FIGS. 6(a) and 6(b) show the state in which the partial non-coated portion 8 is formed at 12 mm or less from the one end.

The non-coated portion 8 is also preferably formed so as to cover a position of 3 mm from the one end of the tubular member 5a. For example, the tubular member 5a shown in FIGS. 5(b), 6(a), and 6(b) is provided with the non-coated portion 8 covering at a position Y of 3 mm from the one end of the tubular member 5a. Alternatively, the non-coated portion 8 may extend toward the one-end side of the tubular member 5a beyond the position Y shown in FIGS. 5(b), 6(a), and 6(b), for example.

The tubular member 5a with the non-coated portion 8 has a shape at least partially narrowed toward the one-end side of the tubular member 5a to further improve insertability into the sheath. As for the narrowed shape, the tubular member 5a with the non-coated portion 8 may be tapered as shown in FIGS. 5(b), 6(a), and 6(b), or may be stepped as shown in FIG. 7(a), for example.

The tubular member 5a with the hydrophilic-coated portion 9 adjacent to the non-coated portion 8 may have a shape at least partially narrowed toward the one end of the tubular member 5a. As for the narrowed shape, the tubular member 5a with the hydrophilic-coated portion 9 may be tapered as shown in FIGS. 5(b), 6(a), and 6(b), or may be stepped as shown in FIGS. 7(a) and 7(b), for example.

As shown in FIGS. 5(b), 6(a), 6(b), 7(a), and 7(b), when the tubular member 5a with the non-coated portion 8 and the tubular member 5a with the hydrophilic-coated portion 9 positioned nearer the other-end side than the non-coated portion 8 are both narrowed, the entire length of the hydrophilic-coated portion 9 is preferably longer than the entire length of the non-coated portion 8. The length here refers to the length of the tubular member 5a in a longitudinal direction Z.

The entire length of the hydrophilic-coated portion 9 refers to the maximum length in the longitudinal direction Z. When there is two or more hydrophilic-coated portions 9, the entire length refers to the total length of the hydrophilic-coated portions 9. For example, when the non-coated portion 8 is not provided on the entire outer periphery of the tubular member 5a as shown in FIG. 6(a), the entire length of the hydrophilic-coated portion 9 refers to the length from the one end to the other end. When the non-coated portion 8 is provided on the entire outer periphery of the tubular member 5a and the hydrophilic-coated portion 9 is divided into two as shown in FIG. 7(a), the entire length of the hydrophilic-coated portion 9 refers to the total length of the divided parts of the hydrophilic-coated portion 9.

Similarly, the entire length of the non-coated portion 8 refers to the maximum length in the longitudinal direction Z.

The outer diameter of the tubular member 5a with the non-coated portion 8 is preferably 1.0 to 1.7 mm, more preferably 1.2 to 1.4 mm.

There is no particular limitation on the outer diameter of the tubular member 5a with the hydrophilic-coated portion 9.

As shown in FIGS. 8(a) and 8(b), an engagement portion 10a or 10b for engagement with the tip of the lacrimal duct tube operative instrument 7 may be provided in the lumen 3 of the tubular member 5a in the vicinity of the opening 2.

The engagement portion 10a or 10b engages with the tip of the lacrimal duct tube operative instrument 7 stored in the lumen 3 through the hole 4 to prevent the tip of the lacrimal duct tube operative instrument 7 from penetrating through the opening 2.

For example, the engagement portion may be the engagement portion 10a formed by changing the thickness of the tubular member 5a to reduce the inner diameter of the lumen 3 as shown in FIG. 8(a), or may be the almost ring-shaped engagement portion 10b smaller in diameter than the lumen 3 formed as shown in FIG. 8(b). The almost ring-shaped (cup-shaped with an open bottom) engagement portion 10b may be formed of any one of various hard materials different from the material for the tubular member 5a, for example, a metal such as stainless steel.

There is no particular limitation on the shape of the engagement portion 10b, and the engagement portion 10b may be tapered to decrease continuously the width vertical to the tube axial direction or may be stepped to decrease stepwise the width vertical to the tube axial direction.

In the lacrimal duct tube 1 of the present invention having the engagement portion 10a or 10b, it is preferred that the hydrophilic-coated portion 9 is formed on the surface of the tubular member 5a at the engagement portion 10a or 10b, and the non-coated portion 8 is formed so as not to overlap the surface of the tubular member 5a at the engagement portion 10a or 10b, as shown in FIGS. 8(a) and 8(b).

The lacrimal duct tube 1 of the present invention is preferably used in the sheath guided endoscopic probing. For example, as shown in FIG. 9, the one end of the lacrimal duct tube 1 is inserted into the open end of a sheath 30, and the non-coated portion 8 and the lumen wall of the sheath 30 engage with each other. Accordingly, the lacrimal duct tube 1 reaches the lacrimal duct obstructed site in conjunction with the movement of the sheath 30, and then is placed at the obstructed site.

In this case, as shown in FIG. 9, to attach the sheath 30 to the one end of the lacrimal duct tube 1, when the inner diameter (DI) of the lumen of the sheath 30 and the outer diameter (DT, not shown) of the tubular member 5a with the non-coated portion 8 satisfy the following relational expression (1):

$$1.00 \leq DT/DI \leq 1.89 \quad (1)$$

the lacrimal duct tube 1 is excellent in insertability and adherence to the sheath 30.

In addition, when the DT/DI preferably satisfies the following relational expression (2):

$$1.20 \leq DT/DI \leq 1.56 \quad (2)$$

more preferably satisfies the following relational expression (3):

$$1.26 \leq DT/DI \leq 1.47 \quad (3),$$

the lacrimal duct tube 1 is further excellent in insertability and adherence to the sheath 30.

EXAMPLES

Example 1

The lacrimal duct tube 1 was fabricated from tubular members 5a-1 to 5a-3 and the connection member 6 configured as shown in Table 1 in a manner described below (the tubular member 5b is the same in configuration as the tubular member 5a, and descriptions thereof will be omitted).

First, the tubular members 5a-1 were welded and connected to the both ends of the connection member 6, and then hydrophilic coating was applied to the surface of the tubular members 5a-1. Then, the non-coated tubular member 5a-2 was set and welded to a tip (free end) of the tubular members 5a-1, and the hydrophilic-coated tubular member 5a-3 was set and welded to a tip of the tubular member 5a-2 in this order to form the tapered shape (for the tapered shape, see FIG. 5(b) showing the non-coated portion 8, and the hydrophilic-coated portion 9 adjacent to the one-end side of the non-coated portion 8, and the hydrophilic-coated portion 9 adjacent to the other-end side of the non-coated portion 8. Table 1 describes the materials, shapes, and others of the members).

After the pairs of tubular members 5a-1 to 5a-3 and the connection member 6 were formed in a string, the holes 4 were formed in the tubular members 5a-3 at 30 mm from the free ends, and then the lumens of the tubular members 5a-3 were reduced in diameter to form the engagement portions.

Then, by cutting the tips (free ends) of the tubular members 5a-3, the tips were formed in the narrowed shape and the tubular members 5a-2 were arranged at 2 to 5 mm from the tips of the tubular members 5a-3 (see FIG. 5(b)).

In this manner, the lacrimal duct tube having the tubular member 5a with the non-coated portion 8 (tubular member 5a-2 portion) over the entire outer peripheral surface was fabricated.

Six kinds of lacrimal duct tubes with outer diameters (DT) of 0.9 mm to 1.4 mm different by 0.1 mm of the portion at 3 mm from the one end of the tubular member 5a were prepared.

TABLE 1

| Component | Material | Outer diameter | Inner diameter | Entire length |
|---|---|---|---|---|
| Tubular member 5a-1 | Thermoplastic polyurethane resin/isobutylene block copolymer = 9/1 | φ1.5 mm | φ0.5 mm | 35 mm |
| Tubular member 5a-2 | | φ0.9 to 1.4 mm *) | φ0.5 mm | 3 mm |
| Tubular member 5a-3 | | φ1.1 mm | φ0.5 mm | 3 mm |
| Connection member 6 | | φ0.8 mm | | 22 mm |

*) Six kinds of tubes with outer diameters different by 0.1 mm

Comparative Example

Three kinds of lacrimal duct tubes were fabricated in the same manner as in the Example 1 except that the hydrophilic-coated portion 9 was formed instead of the non-coated portion 8 and the tubular members 5a and 5b with outer diameters (DT) of 0.9 to 1.1 mm different by 0.1 mm at 3 mm from the one end were used.
(Experimental Example)
A 18G sheath (SurFlow Flash (produced by Terumo Corporation), code number: SR-FS1851 (length: 51 mm, outer diameter: 1.3 mm, inner diameter (DI): 0.95 mm) was used to inspect the lacrimal duct tubes for insertability into the sheath, stable adherence to the same, and load of extraction from the same according to the measurement method below.
(Measurement Method)
1) The 18G sheath (30) was cut from its base, and cut in half at a position of 5 mm from the terminal end on the circumference of circle (see FIG. 10), and then slit vertically to obtain a portion capable of being held by tweezers (reference material: "Journal of the Eye," 29(7), 933 to 940).
2) The sheath produced at 1) was cut to be 35 mm long.
3) The insides of the sheath and the lacrimal duct tube were flushed with saline.
4) A bougie (LACRIFAST (produced by Kaneka Corporation, attachment of catalog number: LF-R105)) was attached to a load meter (digital force gauge FGC-0.5 (produced by NIDEC-Shimpo Corporation)), and then the bougie was inserted into the lacrimal duct tube from the hole.
5) The surface of the lacrimal duct tube was moistened, and then the load of inserting the lacrimal duct tube into the sheath through the opening of the sheath at the holding portion side up to 3 mm from one end of the lacrimal duct tube was measured (insertion load).
6) Then, the bougie was pulled out of the lacrimal duct tube. It was checked whether the lacrimal duct tube bounced out of the sheath at or after the extraction of the bougie (stable adherence).
7) The lacrimal duct tube and the sheath were chucked, and the load of pulling the lacrimal duct tube out of the sheath was measured by the use of a tensile tester (extraction load).

Conditions for the tensile tester were as follows:
Load cell autograph EZ-TEST (produced by Shimadzu Corporation): 20 N
Inter-chuck distance: 20 mm
Table 2 shows the measurement results. Evaluation criteria are as follows:
Judgment (the number of samples N=3)
(Insertability into the Sheath)
◯: Insertable into the sheath up to 3 mm from the tip of the tube
x: Non-insertable into the sheath up to 3 mm from the tip of the tube
(Insertion Load into the Sheath)
◉: Average is 1.5N or more, minimum is 1.5N or more
◯: Average is 1.5N or more, minimum is 1.5N or less
Δ: Average is 1.0N or more, minimum is 1.0N or less
x: Average is 0.5N or more, minimum is 0.5N or less
(Stable Adherence in the Sheath)
◯: When the tubular member is inserted into the sheath from one end, the tubular member does not bounce out of the sheath at or after the extraction of the bougie
x: Instable: When the tubular member is inserted into the sheath from one end, the tubular member may bounce out of the sheath at or after the extraction of the bougie
(Extraction Load from the Sheath)
◯: Average is 1.0N or more, minimum is 1.0N or more
Δ: Average is 1.0N or more, minimum is 1.0N or less
x: Average is 1.0N or less, minimum is 1.0N or less

TABLE 2

| | | Outer diameter | | | | | |
|---|---|---|---|---|---|---|---|
| Test sample | Evaluation | 0.9 mm | 1.0 mm | 1.1 mm | 1.2 mm | 1.3 mm | 1.4 mm |
| With non-coated portion | Possibility of insertion | ◯ | ◯ | ◯ | ◯ | ◯ | ◯ |
| | Insertion load | X | Δ | Δ | ◉ | ◉ | ◉ |
| | Stable adherence | ◯ | ◯ | ◯ | ◯ | ◯ | ◯ |
| | Extraction load | X | Δ | Δ | ◯ | ◯ | ◯ |
| | DT/DI | 0.95 | 1.05 | 1.16 | 1.26 | 1.37 | 1.47 |
| Without non-coated portion (entirely coated) | Possibility of insertion | ◯ | ◯ | ◯ | | | |
| | Insertion load | X | X | X | | | |
| | Stable adherence | ◯ | ◯ | X | | | |
| | Extraction load | X | X | Δ | | | |

It can be seen from the results shown in Table 2 that the lacrimal duct tube with the non-coated portion can be inserted into the sheath under a proper load and is hard to pull out of the sheath with stable adherence, when the outer diameter (DT) of the tubular member at 3 mm from one end is adjusted to 1.0 to 1.4 mm.
Meanwhile, it has been revealed that all of the lacrimal duct tubes of Comparative Example 1 without non-coated portion on the surface of the tubular member could be easily inserted into the sheath under a low insertion load, but could be easily pulled out of the sheath under a low extraction load, and therefore the lacrimal duct tubes of Comparative Example 1 were likely to be pulled out during surgeries.

In some cases, the lacrimal duct tube having the tubular member with an outer diameter of 1.1 mm naturally bounced out of the sheath after the extraction of the bougie.

REFERENCE SIGNS LIST

1 Lacrimal duct tube
2 Opening
3 Lumen
4 Hole
5 Tubular member
6 Connection member
7 Lacrimal duct tube operative instrument
8 Non-coated portion
9 Hydrophilic-coated portion
10 Engagement portion
21 Upper lacrimal punctum
22 Lower lacrimal punctum
23 Upper lacrimal canaliculus
24 Lower lacrimal canaliculus
25 Common canaliculus
26 Lacrimal sac
27 Nasolacrimal duct
28 Inferior nasal meatus
29 Lacrimal endoscope
30 Sheath
31 Lacrimal duct
32 Obstructed site
33 Lacrimal duct tube
X Position of 12 mm from one end of the tubular member 5a
Y Position of 3 mm from one end of the tubular member 5a
Z Longitudinal direction of the tubular member 5a
DT Outer diameter of no-coated portion of tubular member
DI Inner diameter of lumen of sheath

The invention claimed is:

1. A lacrimal duct tube, comprising:
a pair of tubular members that each have at one end an opening communicating with a lumen and have in a wall a hole for guiding a lacrimal duct tube operative instrument to the lumen; and
a connection member that connects the other ends of the tubular members, wherein
surfaces of the tubular members include a hydrophilic-coated portion and a non-coated portion without the hydrophilic coating,
wherein the lumen in the vicinity of the opening includes an engagement portion for engagement with a tip of the lacrimal duct tube operative instrument, and
the non-coated portion is formed without overlapping with the surface of the tubular member at the position of the engagement portion.

2. The lacrimal duct tube according to claim 1, wherein the engagement portion is formed of a resin as a part of material for the tubular member or a material different from the resin, and has an inner diameter smaller than the outer diameter of the tip of the lacrimal duct tube operative instrument.

3. The lacrimal duct tube according to claim 1 or 2, wherein the non-coated portion is partially or entirely formed at 12 mm or less from the one end of the tubular member.

4. The lacrimal duct tube according to claim 1, wherein the outer diameter of the non-coated portion of the tubular member is 1.0 to 1.7 mm.

5. The lacrimal duct tube according to claim 4, wherein the outer diameter of the non-coated portion of the tubular member is 1.2 to 1.4 mm.

6. The lacrimal duct tube according to claim 1, wherein the non-coated portion overlaps the tubular member at a position of 3 mm from the one end of the tubular member.

7. The lacrimal duct tube according to claim 1, wherein the non-coated portion extends over the entire or partial periphery of the tubular member.

8. The lacrimal duct tube according to claim 1, wherein at least part of the tubular member at the non-coated portion is narrowed toward the one end of the tubular member.

9. The lacrimal duct tube according to claim 8, wherein the tubular member at the hydrophilic-coated portion adjacent to the non-coated portion is narrowed toward the one end of the tubular member.

10. The lacrimal duct tube according to claim 9, wherein
the tubular member is narrowed at both the non-coated portion and the hydrophilic-coated portion positioned at the other end side of the non-coated portion, and
at the narrowed tubular member, the entire length of the hydrophilic-coated portion is longer than the entire length of the non-coated portion.

11. The lacrimal duct tube according to claim 1, wherein the maximum outer diameter of the tubular member is 1.4 to 1.7 mm.

12. The lacrimal duct tube according to claim 1, wherein the hole is an insertion opening for an operating bar as the lacrimal duct tube operative instrument or a lacrimal endoscope as the lacrimal duct tube operative instrument.

13. The lacrimal duct tube according to claim 1, wherein, when the one end of the tubular member is inserted into an opening end of a sheath, the non-coated portion and a lumen wall of the sheath engage with each other, and the lacrimal duct tube reaches an obstructed site in a lacrimal duct in conjunction with movement of the sheath and is placed in the obstructed site.

14. The lacrimal duct tube according to claim 13, wherein an inner diameter (DI) of the lumen of the sheath and an outer diameter (DT) of the tubular member at the non-coated portion satisfy the following relational expression (1):

$$1.00 \leq DT/DI \leq 1.89 \tag{1}$$

15. The lacrimal duct tube according to claim 14, wherein the DI and the DT satisfy the following relational expression (2):

$$1.20 \leq DT/DI \leq 1.56 \tag{2}$$

* * * * *